US00PP14835P2

(12) United States Plant Patent
Jonkers

(10) Patent No.: US PP14,835 P2
(45) Date of Patent: May 25, 2004

(54) IMPATIENT PLANT NAMED 'FIFY ORANTWO'

(50) Latin Name: *Impatiens walleriana*
Varietal Denomination: Fify Orantwo

(75) Inventor: Johanna B. Jonkers, Hoorn (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/397,998

(22) Filed: Mar. 25, 2003

(51) Int. Cl.[7] ..... A01H 5/00
(52) U.S. Cl. ..... Plt./317
(58) Field of Search ..... Plt./317

*Primary Examiner*—Bruce R. Campell
*Assistant Examiner*—Michelle Kizilkaya
(74) *Attorney, Agent, or Firm*—Jondle & Associates PC

(57) ABSTRACT

An impatiens cultivar particularly distinguished by orange colored flowers, compact habit and good basal branching.

1 Drawing Sheet

Genus and species: *Impatiens walleriana.*
Variety denomination: 'Fify Orantwo'.

BACKGROUND OF THE NEW PLANT

The present invention comprises a new and distinct cultivar of impatiens, botanically known as *Impatiens walleriana,* and hereinafter referred to by the cultivar name 'Fify Orantwo'. The new cultivar is asexually reproduced from vegetative cuttings and tissue culture resulting from the cross of the seed/pod parent IMR-1527-1, an orange proprietary line that is unnamed and unpatented×IW-736-2, a scarlet proprietary line that is unnamed and unpatented.

'Fify Orantwo' is a product of a planned breeding program intended to create new impatiens plants with orange colored flowers, compact habit, good basal branching and moderately vigorous growth.

The new cultivar was created in 2000 in Andijk, The Netherlands and has been asexually reproduced repeatedly by vegetative cuttings and tissue culture in Gilroy, Calif., Andijk, The Netherlands and Guatemala over a two and half year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new impatiens plant is illustrated by the accompanying photograph which shows blooms, buds, and foliage of the plant in full color, the colors shown being as true as can be reasonably obtained by conventional photographic procedures.

The photograph shows the mature inflorescence.

DESCRIPTION OF THE NEW CULTIVAR

The following detailed descriptions set forth the distinctive characteristics of 'Fify Orantwo'. The data which defines these characteristics were collected from asexual reproductions carried out in Gilroy, Calif. The plant history was taken on 6 month old plants grown in 5-inch pots, in a poly-covered greenhouse under natural light in the fall/winter season and color readings were taken in that greenhouse in the winter season. Plants had been cut back numerous times prior to data readings taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Impatiens walleriana.*
*Commercial.*—Impatiens.
Form: Compact, small mounded.
Growth and branching habit: Compact habit, good basal branching, moderately vigorous, pinching of the terminal apices enhances branching.
Height: From soil level to top of blooms: Approximately 10–20 cm.
Width: Approximately 30–35 cm including flowers.
Time to produce a finished flowering plant: 8–10 weeks for a 4-inch pot.
Outdoor plant performance: Shade, free-flowering all year, some heat tolerance. Use in mixed containers, window boxes and mass plantings.
Time to initiate and develop roots: Approximately 10–21 days in the greenhouse.
Root description: Fibrous, fleshy, white.

THE LEAVES

Arrangement: Alternate.
Length: 3.0–3.5 cm.
Width: 1.9–2.3 cm.
Leaf blade shape: Ovate.
Leaf margin: Crenate with ciliate (1) between each lobe.
Apex aspect: Cuspidate with one ciliate at the tip.
Base aspect: Acuminate.
Foliage color: Upper side, RHS 147A (yellow-green) but little darker; Underside, RHS 147B (yellow-green) with 137B (green) mid-vein.
Foliage texture: Glabrous.
Venation: Pinnate.
Venation color: RHS 145C (green), fading into the leaf until almost disappearing.

Petiole length: 0.7–1.7 cm.
Petiole diameter: 0.15–0.2 cm.
Petiole color: RHS 145C (green).
Petiole texture: Glabrous.

THE STEM

Length: 10–20 cm.
Diameter: 0.3–0.4 cm.
Internode length: 0.2–0.4 cm.
Color: RHS 144A (yellow-green).
Texture: Glabrous.
Stem anthocyanin: No.
Pedicel diameter: 0.1 cm.
Pedicel length: 1.1–2.0 cm.
Pedicel color: RHS 144A (yellow-green) little lighter.
Peduncle length: 1.7–3.0 cm.
Peduncle diameter: 0.15–0.2 cm.
Peduncle color: RHS 144A (yellow-green) little lighter.
Peduncle texture: Glabrous.

THE BUD

Shape: Ovate.
Diameter: 0.3–0.4 cm.
Length: 0.4–0.7 cm.
Color at tight bud: RHS 47C (red) mingling of different intensities.

THE FLOWER

Blooming habit: Continuous and freely all through the year.
Inflorescence type: Racemes in leaf axis.
Number of flowers per raceme and/or whorl: 10–20 including buds.
Floret form and a number of petals: 5; 1 standard or dorsal (free), 2 lateral or lobed pairs (wing petals) deeply lobed.
Flower color: Upper side, dorsal petal RHS N30A (orange-red); lateral petals RHS N30A (orange-red).
Flower color: Underside, dorsal petal is RHS 40C (red) with a keel RHS 145D (yellow-green); lateral RHS 40C (red).
Floret diameter: 2.4–2.6 cm; height 2.4–2.8.
Petal size, dorsal: Length 0.9–1.0 cm; width 1.0–1.1 cm; shape orbicular; apex shape retuse. Lateral petal size: length 1.5 cm; width 0.8–0.9 cm; shape obovate; apex shape retuse.
Petal base shape: Fused.
Petal margin: Entire.
Petal texture: Papillose and an iridescent sheen.
Sepals: Three, one larger than the others with a spur.
Large sepal: Color RHS N155B (white) base color with a slight blush of RHS 51C (red) and spot of RHS 53C (red) at the spur; length 0.7–0.9 cm; width 0.6–0.7 cm; shape ovate; apex shape cuspidate; base shape fused.
Spur color: RHS 31C (orange-red) was in indeterminate green hue intermingled; length 2.9–3.1 cm.
Small sepal: Color is RHS 144A (yellow-green); length 0.2 cm; width 0.1 cm; shape ovate; apex shape acute; base shape fused yes.
Sepal texture: Glabrous.
Lastingness of individual blooms: 4–8 days.
Fragrance: None.

THE REPRODUCTIVE ORGANS

Stamens: 5; more or less fused by the anthers, and covering the ovary; color RHS 43A (orange-red) (pollen cap); pollen amount not observed; pistil one complete; fruit seed set not observed.

DISEASE AND INSECT RESISTANCE

Not observed.

COMPARISON WITH KNOWN CULTIVARS

'Fify Orantwo' differs from the female parent in the following ways. The female flowers are a little larger and the habit is not as compact as the Fify Orantwo.

'Fify Orantwo' differs from the male parent in the following ways. The male has a normal sized flower and habit and is a scarlet flowered and Fify Orantwo is orange and a compact plant.

I claim:

1. A new and distinct cultivar of impatiens plant as shown and described herein.

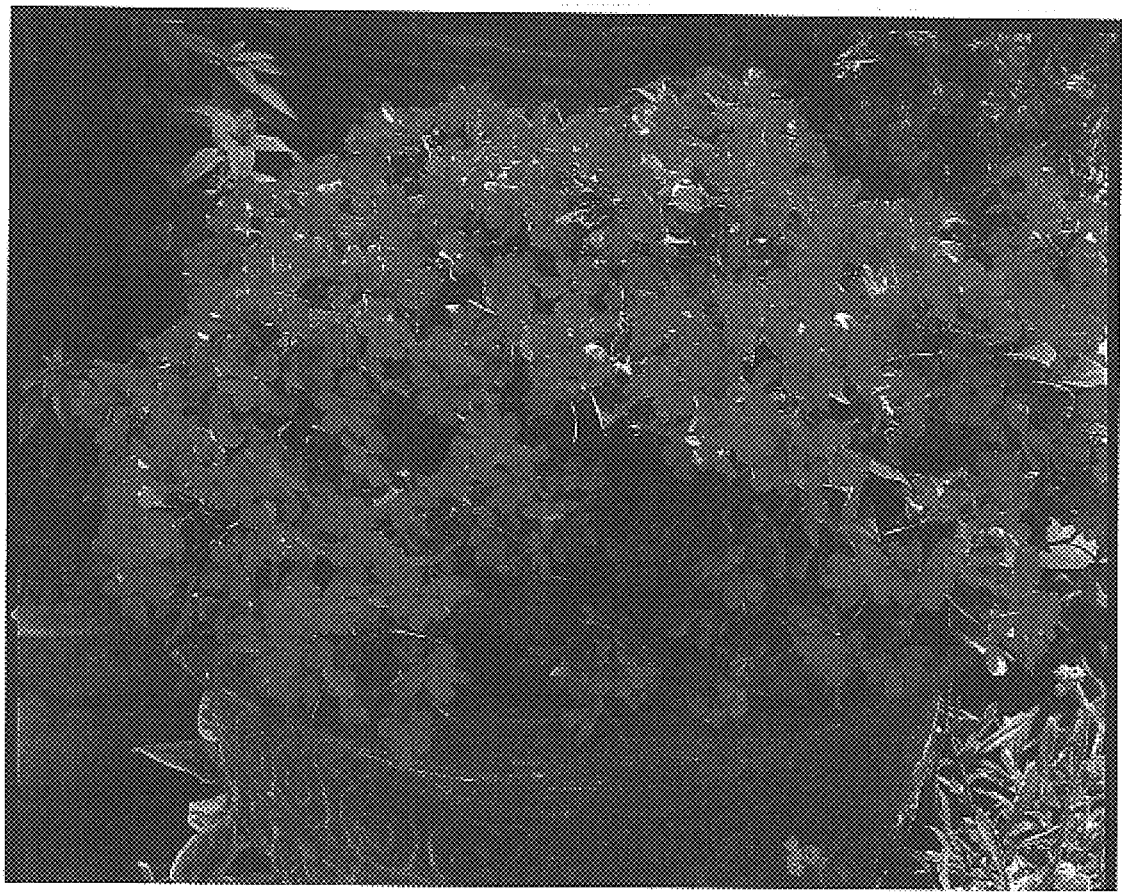

* * * * *